United States Patent
Thieme-Marti (10) Patent No.: US 9,091,391 B2
(45) Date of Patent: Jul. 28, 2015

(54) SIX DEGREES OF FREEDOM MOTION PLATFORM

(75) Inventor: Stefan Jochem Thieme-Marti, Windisch (CH)

(73) Assignee: Varian Medical Systems International AG, Zug (CH)

(*) Notice: Subject to any disclaimer, the term of this patent is extended or adjusted under 35 U.S.C. 154(b) by 970 days.

(21) Appl. No.: 12/896,544

(22) Filed: Oct. 1, 2010

(65) Prior Publication Data

US 2012/0080578 A1    Apr. 5, 2012

(51) Int. Cl.
*B25J 9/00* (2006.01)
*F16M 11/04* (2006.01)
*F16M 11/12* (2006.01)
*F16M 11/18* (2006.01)
*F16M 11/40* (2006.01)
*A61N 5/10* (2006.01)
*A61B 6/04* (2006.01)

(52) U.S. Cl.
CPC ........... *F16M 11/043* (2013.01); *A61N 5/1049* (2013.01); *F16M 11/12* (2013.01); *F16M 11/18* (2013.01); *F16M 11/40* (2013.01); *A61B 6/0407* (2013.01)

(58) Field of Classification Search
CPC .... B25J 9/0078; B25J 17/0266; F16M 11/12; F16M 11/18
USPC ......... 248/550, 560, 581, 583, 599, 600, 601, 248/652, 133, 396, 176.3; 414/735; 74/490.04
See application file for complete search history.

(56) References Cited

U.S. PATENT DOCUMENTS 4,666,362 A * 5/1987 Landsberger et al. ........ 414/735
6,840,127 B2 * 1/2005 Moran ....................... 74/490.04
7,367,772 B2 * 5/2008 Khajepour et al. ........... 414/735

OTHER PUBLICATIONS

"4D Phantom, a uniquely capable 4D QA system," Radiation Oncology Technology Center, Washington University 4D Phantom, downloaded on Sep. 30, 2010 from radonc.wustl.edu/.../4dphantom.html, pp. 1-3.
D. Stewart, "A Platform with Six Degrees of Freedom," Proc Instn Mech Engrs 1965-66, vol. 180 Pt 1 No. 15, pp. 371-386.

* cited by examiner

*Primary Examiner* — Jeanette E Chapman
*Assistant Examiner* — Daniel Kenny
(74) *Attorney, Agent, or Firm* — Patent Law Group LLP; David C. Hsia (57) ABSTRACT

A motion platform includes a base, a platform, and a suspension supporting the platform above the base. Strings preload the platform toward the base while the suspension pushes the platform away from the base. Actuators pull and release the strings to manipulate the platform in multiple degrees of freedom.

26 Claims, 5 Drawing Sheets

SIX DEGREES OF FREEDOM MOTION PLATFORM

FIELD OF INVENTION

This invention relates to a six degrees of freedom (6DoF) motion platform for any application where a device can be controllably and reproducibly moved up to 6DoF.

DESCRIPTION OF RELATED ART

Motion simulators and motion platforms have many applications, including machine tool technology, crane technology, underwater research, air-to-sea rescue, satellite dish positioning, telescopes, flight simulation, and medical procedures. Some motion platforms provide movement up to six degrees of freedom: three rotational degrees of freedom and three translational or linear degrees of freedom.

Radiation therapy, also known as radiation oncology, is the medical use of ionizing radiation to destroy cancer cells in a malignant tumor. Radiation therapy works by damaging the genetic makeup of cells in the area of the body being treated, making it difficult for them to multiply and eventually causing them to die. The goal of radiation therapy is twofold: to destroy as many cancer cells as possible while limiting harm to surrounding healthy tissue.

Treatment planning is the process in which a team consisting of radiation oncologists, radiation therapists, medical physicists, and medical dosimetrists plan the appropriate radiation therapy treatment technique for a patient with cancer. A four-dimensional (4D) treatment plan accounts for the spatial contour of the malignant tumor and its surrounding over time in order to address any interfraction and intrafraction motions. Such a 4D treatment plan may use gating, which delivers radiation only when the malignant tumor passes through a specific window. For evaluation and validation, the 4D treatment plan is practiced on a radiological phantom manipulated by a motion platform to simulate patient movement.

SUMMARY

In one or more embodiments of the present disclosure, a motion platform includes a base, a platform, and a suspension supporting the platform above the base. Flexible links preload the platform toward the base while the suspension pushes the platform away from the base. Actuators pull and release the flexible links to manipulate the platform in multiple degrees of freedom.

BRIEF DESCRIPTION OF THE DRAWINGS

In the drawings.

Use of the same reference numbers in different figures indicates similar or identical elements.

DETAILED DESCRIPTION OF THE INVENTION

Figure 1:
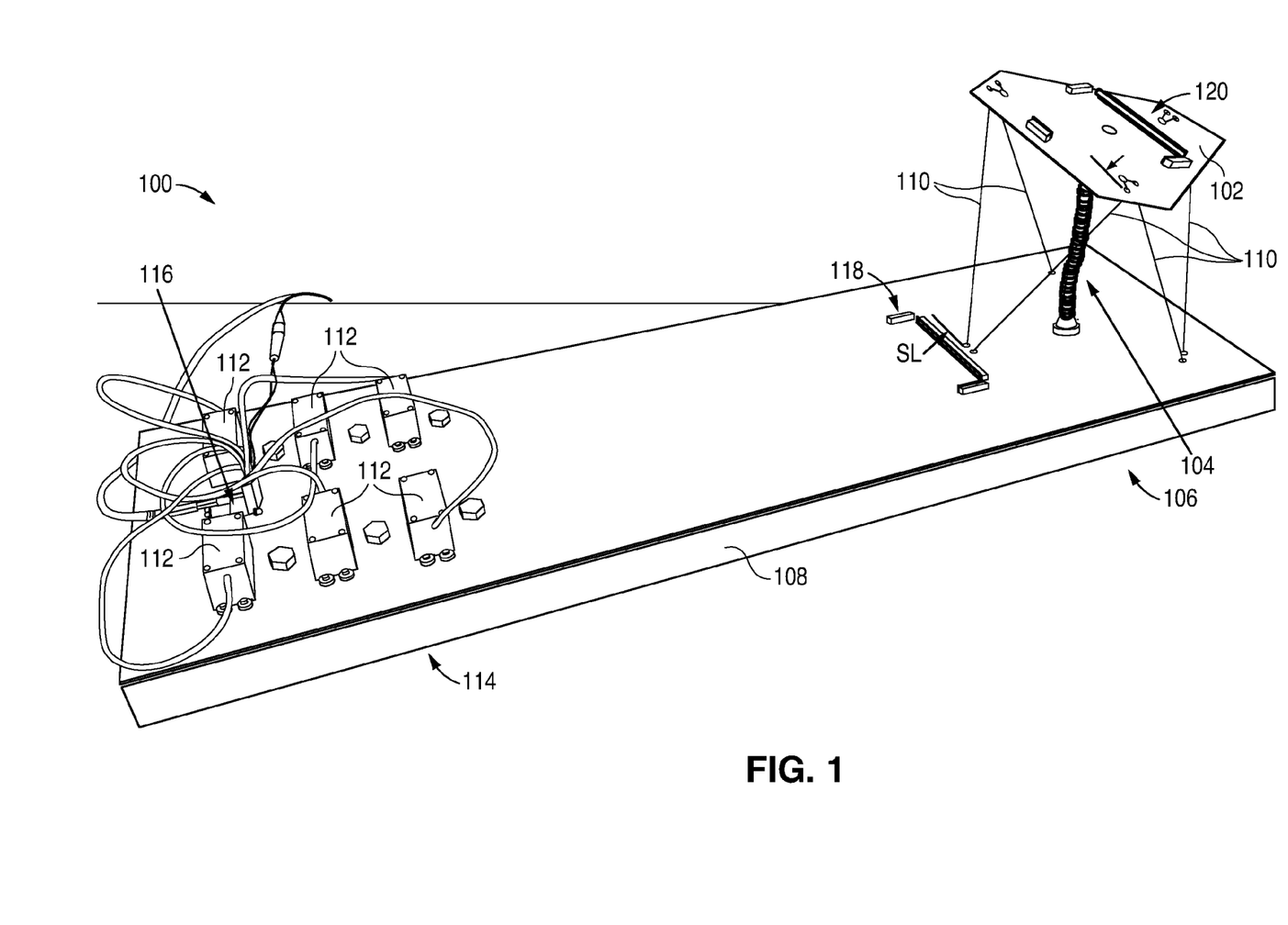
FIG. 1 shows a multiple degrees of freedom motion platform with a moving platform supported by a suspension above a base in one or more embodiments of the present disclosure.

FIG. 1 shows a multiple degrees of freedom motion platform system 100 in one or more embodiments of the present disclosure. Motion platform 100 includes a moving platform 102 supported by a suspension 104 above one section 106 of a base 108 (e.g., one end of base 108). Tensioned strings 110 or other flexible links preload moving platform 102 toward base 108 against suspension 104, which is biased to push the moving platform away from base 108. This configuration provides multiple degrees of freedom to moving platform 102, such as six degrees of freedom with translation and rotation about three perpendicular axes.

Figure 7:
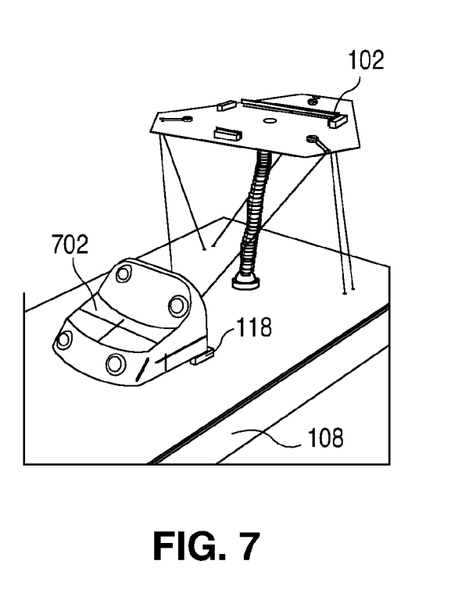
FIG. 7 shows a marker block placed at a reference position for the base of FIG. 1 in one or more embodiments of the present disclosure.

Moving platform 102 is manipulated by six strings 110, which are controlled by six actuators 112 located at another section 114 of base 106 (e.g., an opposite end of base 108). Actuators 112 are driven by a controller 116, which may be a computer or a controller card programmed by a computer. Base 106 includes a reference holder 118 having multiple rails for receiving a reference marker block 702 (FIG. 7). Moving platform 102 includes a sample holder 120 having multiple rails for receiving a sample, such as a reference marker block 702 or a radiological phantom.

In one or more embodiments of the present disclosure, system 100 is exposed to radiation from a radiation therapy or diagnostic machine or magnetic field from a magnetic resonance imaging (MRI) machine. In these embodiments, actuators 112, controller 116, and any other electronics are located away from the radiation or the magnetic field. In these embodiments, moving platform 102, suspension 104, section 106 of base 108, and strings 110 are magnetically inert and/or nonmetallic so they do not interfere with the radiation or the magnetic field, and they are also radio hard so they do not deteriorate under repeated exposures to radiation.

Figure 2:
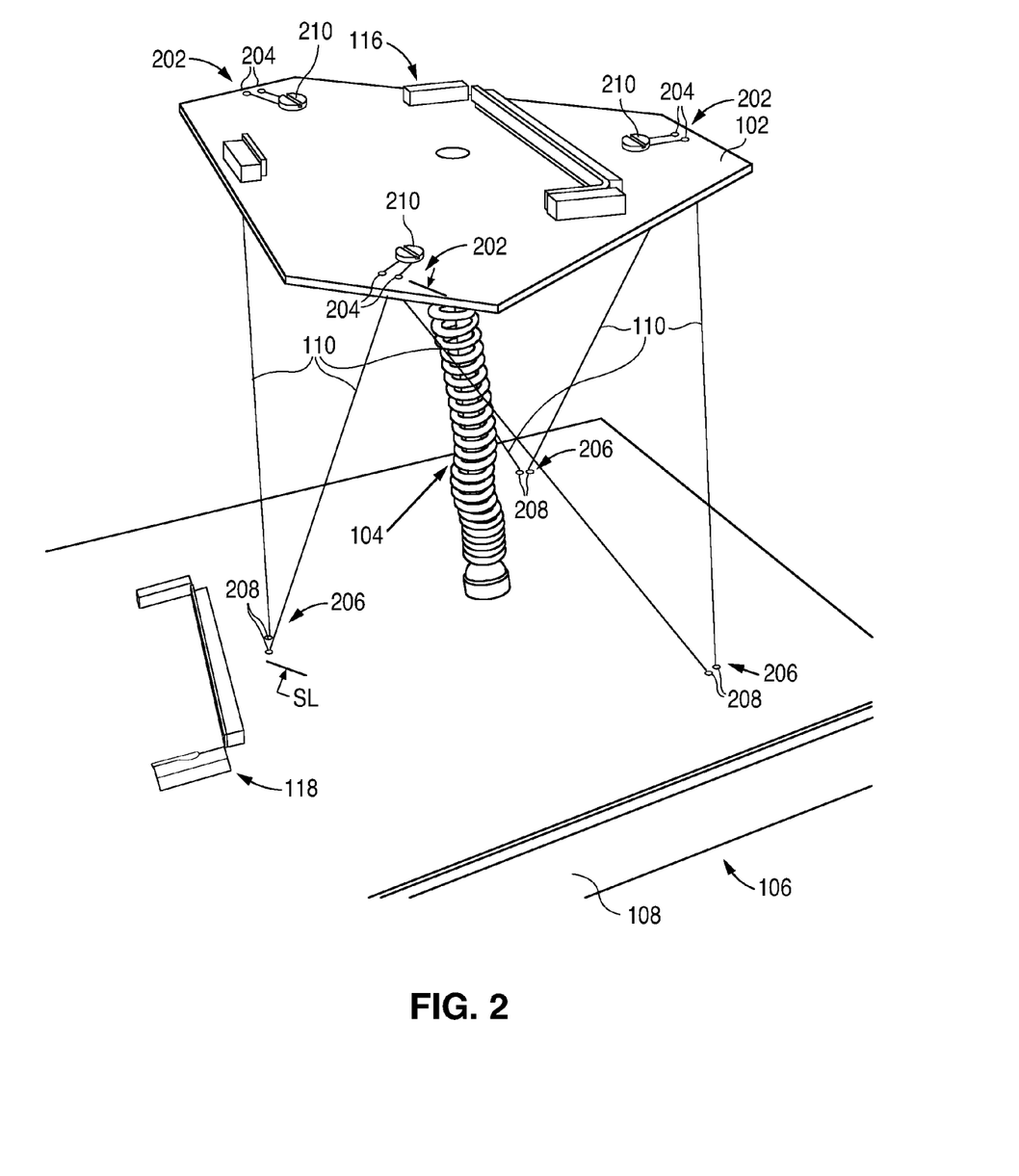
FIG. 2 shows an enlarged view of the moving platform, the suspension, and the base of FIG. 1 in one or more embodiments of the present disclosure.

FIG. 2 shows an enlarged view of moving platform 102, suspension 104, and section portion 106 of base 108 in one or more embodiments of the present disclosure. Moving platform 102 has control points 204 connected to strings 110, and base 106 has control points 208 for receiving strings 110 from control points 204. In one or more embodiments, six control points 204 are divided into three control point pairs 202 and six control points 208 are divided into three control point pairs 206. In each control point pair, the control points may be located close together to provide a stable mechanical configuration. Control point pairs 202 may be located about vertices of an equilateral triangle, and control point pairs 206 of control points 208 may be located about vertices of another equilateral triangle. Control points 204 may be implemented as holes that strings 110 pass through to be secured by a screw 210 on moving platform 102. Control points 208 may also be implemented as holes that strings 110 pass through to the backside of base 108.

From each pair 202 of control points 204, a pair of strings 110 diverges to control points 208 at separate but adjacent pairs 206. From control points 208, strings 110 travel under base 108 to actuators 112 (FIG. 1). As mentioned above, strings 110 preload moving platform 102 toward base 108 against suspension 104, which is biased to push the moving platform away from base 108. In this configuration, the six degrees of freedom (6DoF) position of moving platform 102 is determined by string lengths SL between six pairs of control points 204 and 208. For simplicity, only one string length SL is labeled. Actuators 112 pull and release strings 110 to change string lengths SL and thereby manipulate moving platform 102 with 6DoF motion. Furthermore, a seventh degree of freedom in time may be provided as the 6DoF position changes over time.

Figure 3:
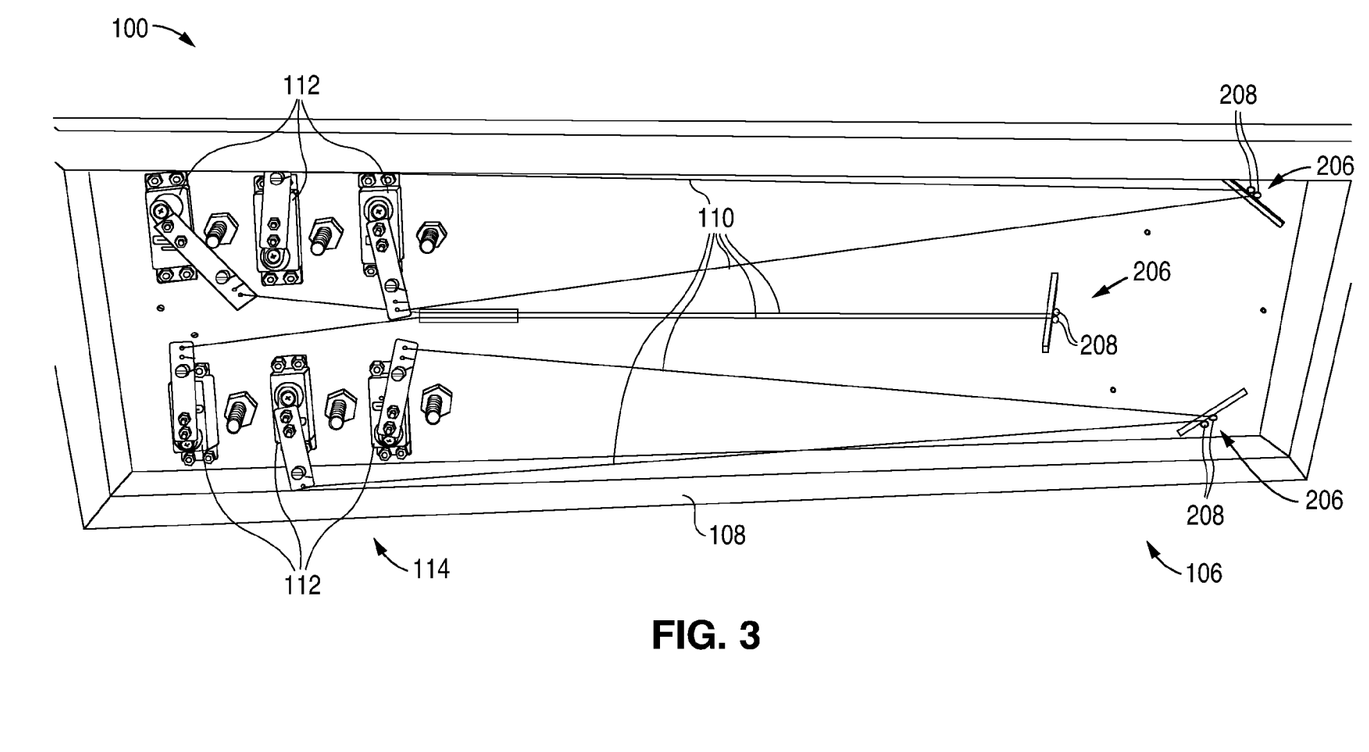
FIG. 3 shows the backside of the motion platform of FIG. 1 in one or more embodiments of the present disclosure.

FIG. 3 shows the backside of motion platform 100 in one or more embodiments of the present disclosure. As described above, strings 110 travel from control points 208 to actuators 112. Actuators 112 can be arranged in a three-by-two array where each has an actuator arm tied to a different string 110 or in other array configurations. To prevent strings 110 from becoming entangled, the left and the rightmost actuators 112 may have their actuator arms pointed inward while the intermediate actuators 112 may have their actuator arms pointed outward, and carbon tubes 302 may be provided so strings 110 for the leftmost actuators 112 are located above strings 110 for the rightmost actuators 112.

Figures 4, 5:
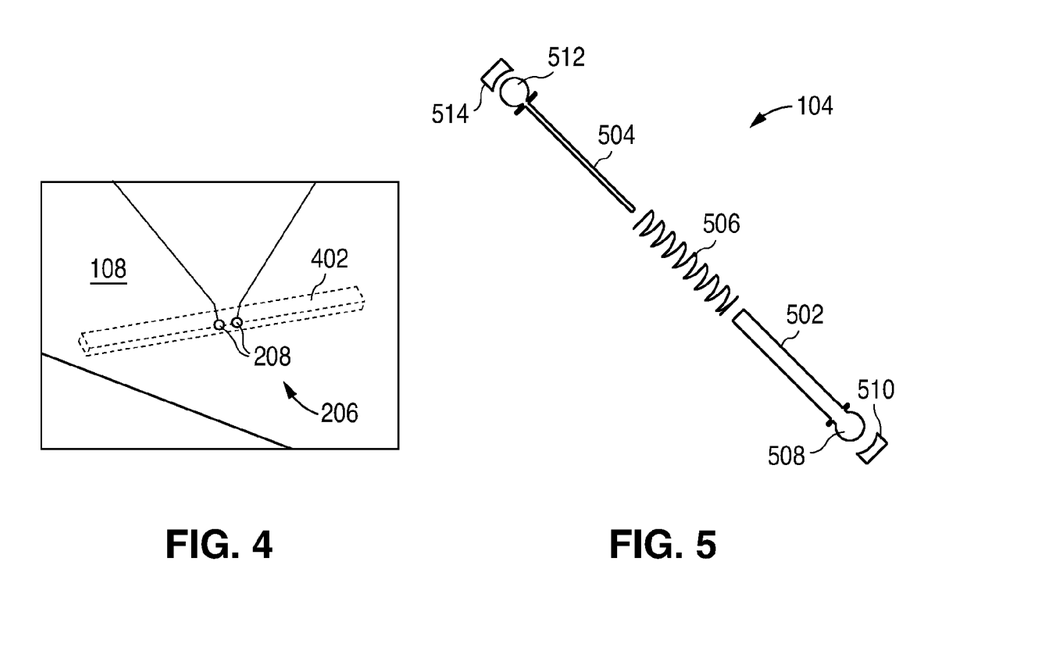
FIG. 4 shows an enlarged top view of control points implemented with guide holes in the base of FIG. 1 in one or more embodiments of the present disclosure.
FIG. 5 shows an exploded view of the suspension of FIG. 1 in one or more embodiments of the present disclosure.

FIG. 4 shows an enlarged top view of a pair 206 of control points 208 in base 108 in one or more embodiments of the present disclosure. A semicircular carbon slat 402 is provided on the other side adjacent to control points 204 for the turn by strings 110 towards actuators 112.

FIG. 5 shows an exploded view of suspension 104 in one or more embodiments of the present disclosure. Suspension 104 may be a prismatic joint having a cylinder 502, a rod 504 received in the cylinder, and a spring 506 that pushes apart the cylinder and the rod. Other suspension configurations known in the art may also be used. For example, instead of spring 506, cylinder 502 and rod 504 may be separated by a pressurized gas or liquid. Cylinder 502 includes an end 508 that forms part of a joint with a counterpart 510 fixed on top of base 108. Rod 504 includes an end 512 that forms a part of a joint with a counterpart 514 fixed to the bottom of moving platform 102. These joints may be spherical joints, universal joints, needle joints, or other joints that allow rotation along three axes.

System 100 of FIG. 1 has low demand on manufacturing accuracy and string slack. To accurately predict a 6DoF position of moving platform 102, system 100 utilizes accurate placement of control points 204 and 208 and the attachment points of suspension 104 to moving platform 102 and base 108. Once system 100 is assembled, it is calibrated to find the relationship between actuator control values, such degrees of arm rotation, and corresponding string lengths SL between control points 204 and 208. Knowing the relationships between the actuator control values and string lengths SL allows for calculation of the required actuator control values for any given 6DoF position of moving platform 102 based on the known geometry of system 100.

Figure 6:
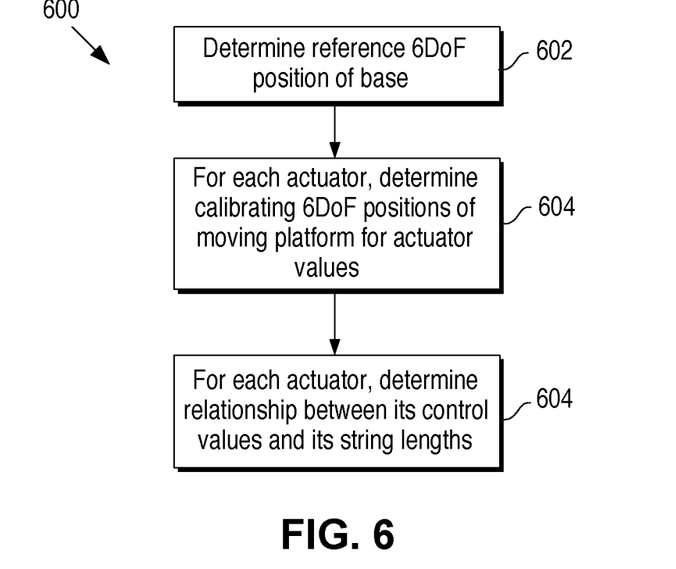
FIG. 6 is a flowchart for calibrating the motion platform of FIG. 1 in one or more embodiments of the present disclosure.

FIG. 6 is a flowchart of a method 600 for calibrating motion platform 100 of FIG. 1 in one or more embodiments of the present disclosure. Although the blocks of method 600 and any subsequent method are illustrated in a sequential order, these blocks may also be performed in parallel, and/or in a different order than those described herein. Also, the various blocks may be combined into fewer blocks, divided into additional blocks, and/or eliminated based upon the desired implementation.

In block 602, a reference 6DoF position of base 108 is determined. As shown in FIG. 7, the reference 6DoF position is determined by placing an optical reference marker block 702 in reference holder 118 of base 108, capturing reference images of the reference marker block with a measuring stereo camera, and calculating the reference 6DoF position from the reference images with a computer. The measurement may be in any coordinate system and there is no special requirement for the placement of the measuring stereo camera. Instead of using an optical reference system, a radio frequency (RF) transponder and a RF tracking system may be used. Referring back to FIG. 6, block 602 may be followed by block 604.

Figure 8:
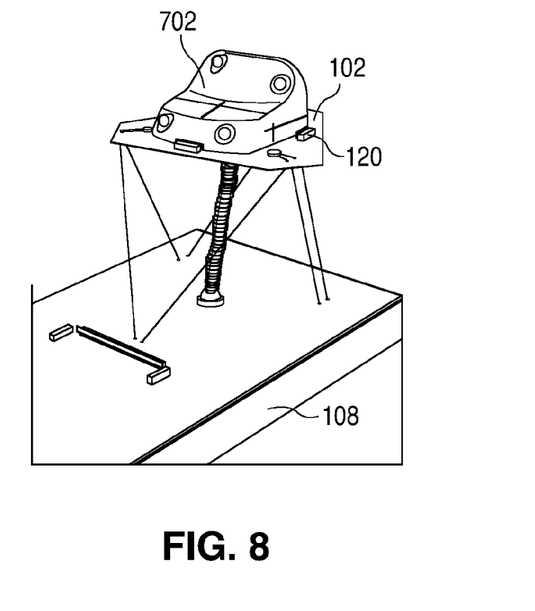
FIG. 8 shows the marker block placed at a calibrating position for the moving platform of FIG. 1 in one or more embodiments of the present disclosure.

In block 604, the relationships between actuator control values and string lengths SL for actuators 112 are determined one actuator at a time. A set of control values is provided to the one actuator 112 being calibrated while the control values for the other actuators 112 are held constant. A calibrating 6DoF position of moving platform 102 is determined at each control value. As shown in FIG. 8, the calibrating 6DoF position is determined by placing reference marker block 702 in sample holder 120 of moving platform 102, capturing calibrating images of the reference marker block with the measuring stereo camera, and calculating the calibrating 6DoF position from the calibrating images with the computer.

With the calibrating 6DoF positions and the reference 6DoF position, string lengths SL at the control values of the one actuator 112 being calibrated are determined with a computer from the known geometry of reference marker 702, control points 204 and 208, and the attachment points of suspension 104. String lengths SL for the other actuators 112 are also determined even though they should remain constant if the geometry of system 100 is perfectly known. Any variation in the "constant" string lengths SL for the other actuators 112 may be used with an optimization program to correct assumption of the geometry of system 100, thereby reducing the production tolerance. The corrected geometry may then be used to recalibrate the relationships between the actuator control values and string lengths SL.

The relationships of actuator control values and string lengths SL may be saved in a data structure. In operation, the string lengths SL for a desired 6DoF position are determined from the known geometry of system 100 and then converted into corresponding control values for actuators 112 to manipulate moving platform 102 to the desired 6DoF position.

Figure 9:
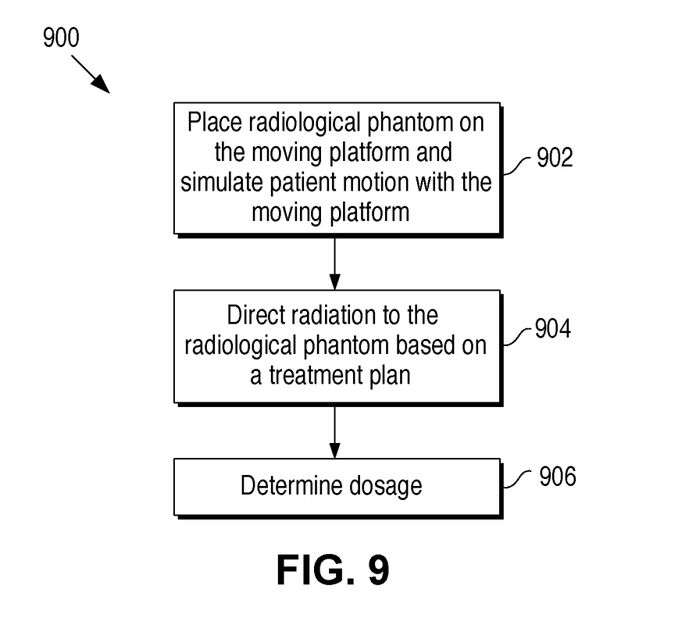
FIG. 9 is a flowchart for operating the motion platform of FIG. 1 in one or more embodiments of the present disclosure.

FIG. 9 is a flowchart of a method 900 for operating motion platform 100 of FIG. 1 in one or more embodiments of the present disclosure. While motion platform 100 may be used for many applications, use in radio therapy is provided for illustrative purposes.

In block 902, a radiological phantom is placed in sample holder 120 on moving platform 102 and actuators 112 begin to manipulate the moving platform to simulate patient motion. The patient motion may be captured over time beforehand using another system and then programmed by into controller 116 for driving actuators 112 to simulate the patient motion. The radiological phantom may include a two-dimensional (2D) or three-dimensional (3D) dose verification device. Alternatively a 2D or 3D dose verification device is placed on moving platform 102 along with the radiological phantom.

A 4D imaging modality is used to capture images of the radiological phantom under the simulated patient motion. The 4D imaging modality may be a computed tomography (4DCT), a cone beam CT (4DCBCT), a positron emission tomography (4DPET), a 4D single photon emission computed tomography (4DSPECT), a 4DMRI, or a fluoroscopy. Block 902 may be followed by block 904.

In block 904, a radiation therapy machine directs radiation to the radiological phantom based on a treatment plan and positional information from the 4D imaging modality. Block 904 may be followed by block 906. Alternatively radiation may be delivered to the radiological phantom to verify tracking provided by the 4D imaging modality.

In block 906, dose measurements are determined from the dose verification device for evaluating and validating the treatment plan. Alternatively dose measurements are determined to verify tracking provided by the 4D imaging modality. Instead of dose measurements, materials detectable by a positional tracking system may be present in the radiological phantom and used to verify tracking by the 4D imaging modality.

Various other adaptations and combinations of features of the embodiments disclosed are within the scope of the invention. Although system 100 has been described with respect to radiation therapy, it may be used for any application where a device has to be moved in controlled and reproducible way in up to 6DoF. Other configurations of control points 204 on moving platform 102 and control points 208 on base 108 may be used. For example, control points 204 may be located about vertices of a hexagon, and control points 208 may also be located about vertices of another hexagon. Other types of suspension 104 may be used. For example, suspension 104 may be an air bed with jets of air supporting moving platform 102 above base 108. Numerous embodiments are encompassed by the following claims.

The invention claimed is:

1. A motion platform, comprising:
a base comprising a first section and a second section horizontally separated by an intermediate section between the first and the second sections, the first, the second, and the intermediate sections being fixed relative to each other;
a platform;
a suspension supporting the platform to enable a range of motion of the platform above the first section of the base but not the second section of the base;
actuators located at the second section of the base to be horizontally offset from the platform above the first section of the base; and
flexible links connecting the actuators to the platform to provide motion in multiple degrees of freedom to the platform.

2. The motion platform of claim 1, wherein the flexible links are strings under tension that preload the platform toward the base and the suspension is biased to push the platform away from the base.

3. The motion platform of claim 1, wherein:
the flexible links travel from first control points on the platform down to second control points on the base, and from the second control points to the actuators to provide motion in six degrees of freedom to the platform.

4. A motion platform, comprising:
a base comprising a first section and a second section horizontally separated by an intermediate section between the first and the second sections;
a platform;
a suspension supporting the platform above the first section of the base;
actuators located at the second section of the base to be horizontally offset from the platform above the first section of the base; and
flexible links connecting the actuators to the platform to provide motion in multiple degrees of freedom to the platform, wherein:
the flexible links travel from first control points on the platform down to second control points on the base, and from the second control points to the actuators to provide motion in six degrees of freedom to the platform;
the first control points comprise three pairs of control points on the platform;
the second control points comprise three pairs of holes in the base;
the flexible links travel from the three pairs of control points on the platform down through the three pairs of holes, under the base and back to the actuators at the second section of the base; and
from each pair of control points, a pair of the flexible links diverges to holes at separate but adjacent pairs of holes.

5. The motion platform of claim 1, wherein the suspension comprises a spring-loaded prismatic joint having a first end coupled by a first joint to the base and a second end coupled by a second joint to the platform.

6. The motion platform of claim 5, wherein the base, the suspension, the platform, and the flexible links are at least one of magnetically inert and nonmetallic.

7. The motion platform of claim 5, wherein the first and the second joints allow rotation along three axes.

8. The motion platform of claim 1, wherein the platform further comprises a holde for a radiological sample or a reference marker.

9. The motion platform of claim 8, wherein the base further comprises another holder for the reference marker near the first section of the base and proximate to the platform.

10. The motion platform of claim 1, further comprising a controller coupled to the actuators.

11. The motion platform of claim 1, wherein the suspension comprises an air bed with jets of air supporting the platform above the base.

12. The motion platform of claim 1, wherein the base comprises an elongated base where the first and the second sections are distal sections at different ends of the base separated by the intermediate section.

13. The motion platform of claim 12, wherein all actuators in the motion platform are located at the second section of the base.

14. A motion platform, comprising:
a base comprising a first section and a second section horizontally separated by an intermediate section between the first and the second sections, the first, the second, and the intermediate sections being fixed relative to each other;
a platform;
a supporting means for enabling a range of motion to the platform above the first section of the base but not the second section of the base;
actuating means for providing motion in multiple degrees of freedom to the platform, the actuating means being located at the second section of the base to be horizontally offset from the platform above the first section of the base; and
linking means for connecting the actuating means to the platform.

15. The motion platform of claim 14, wherein the linking means are strings under tension that preload the platform toward the base and the supporting means is biased to push the platform away from the base.

16. The motion platform of claim 14, wherein:
the linking means travel from first control points on the platform down to second control points on the base, and from the second control points to the actuating means to provide motion in six degrees of freedom to the platform.

17. The motion platform of claim 14, wherein the supporting means comprises a spring-loaded prismatic joint having a first end coupled by a first joint to the base and a second end coupled by a second joint to the platform.

18. The motion platform of claim 17, wherein the base, the supporting means, the platform, and the linking means are at least one of magnetically inert and nonmetallic.

19. The motion platform of claim 17, wherein the first and the second joints allow rotation along three axes.

20. The motion platform of claim 14, wherein the platform further comprises a holder for a radiological sample or a reference marker.

21. The motion platform of claim 20, wherein the base further comprises another holder for the reference marker near the first section of the base and proximate to the platform.

22. The motion platform of claim 14, further comprising a control means for controlling the actuating means.

23. The motion platform of claim 14, wherein the supporting means comprises an air bed with jets of air supporting the platform above the base.

24. The motion platform of claim 14, wherein the base comprises an elongated base where the first and the second sections are distal sections at different ends of the base separated by the intermediate section.

25. The motion platform of claim 24, wherein all actuating means in the motion platform are located at the second section of the base.

26. A motion platform, comprising:
a base comprising a first section and a second section horizontally separated by an intermediate section between the first and the second sections;
a platform;
a supporting means for supporting the platform above the first section of the base;
actuating means for providing motion in multiple degrees of freedom to the platform, the actuating means being located at the second section of the base to be horizontally offset fron the platform above the first section of the base; and
linking means for connecting the actuating means to the platform, wherein:
the linking means travel from first control points on the platform down to second control points on the base, and from the second control points to the actuating means to provide motion in six degrees of freedom to the platform;
the first control points comprise three pairs of control points on the platform;
the second control points comprise three pairs of holes in the base;
the linking means travel from the three pairs of control points on the platform down through the three pairs of holes, under the base and back to the actuating means at the second section of the base; and
from each pair of control points, a pair of the linking means diverges to holes at separate but adjacent pairs of holes.

* * * * *

UNITED STATES PATENT AND TRADEMARK OFFICE
CERTIFICATE OF CORRECTION

| | | |
|---|---|---|
| PATENT NO. | : 9,091,391 B2 | Page 1 of 1 |
| APPLICATION NO. | : 12/896544 | |
| DATED | : July 28, 2015 | |
| INVENTOR(S) | : Stefan Jochem Thieme-Marti | |

It is certified that error appears in the above-identified patent and that said Letters Patent is hereby corrected as shown below:

In the Claims

Column 6
Line 30, Claim 8, where "holde" should read --holder--.

Signed and Sealed this
Eighth Day of December, 2015

Michelle K. Lee
*Director of the United States Patent and Trademark Office*